United States Patent [19]

Gristina

[11] 4,229,840
[45] Oct. 28, 1980

[54] TOTAL TRISPHERICAL WRIST PROSTHESIS

[75] Inventor: Anthony G. Gristina, Winston-Salem, N.C.

[73] Assignee: Pfizer Inc., New York, N.Y.

[21] Appl. No.: 929,915

[22] Filed: Aug. 1, 1978

[51] Int. Cl.³ .............................................. A61F 1/03
[52] U.S. Cl. ................................. 3/1.91; 128/92 C
[58] Field of Search ................. 3/1.91, 1.912, 1.913; 128/92 C, 92 CA

[56] References Cited

U.S. PATENT DOCUMENTS

| | | | |
|---|---|---|---|
| 4,003,095 | 1/1977 | Gristina | 3/1.91 |
| 4,040,130 | 8/1977 | Laure | 3/1.91 |
| 4,040,131 | 8/1977 | Gristina | 3/1.91 |
| 4,063,314 | 12/1977 | Loda | 3/1.91 |
| 4,179,758 | 12/1979 | Gristina | 3/1.91 |

*Primary Examiner*—Clifford D. Crowder
*Attorney, Agent, or Firm*—Connolly and Hutz

[57] ABSTRACT

The prosthesis includes two components having biocompatible metal balls at one end thereof. The radial component is secured by an affixation to the distal radius. The metacarpel component is implanted by a pair of affixation stems into the second and third metacarpel bones of the hand. The balls are rotatably captured between a pair of cutout plastic spheroidal blocks clamped together by a biocompatible metal shell, which is spacially compatible within the wrist area.

9 Claims, 5 Drawing Figures

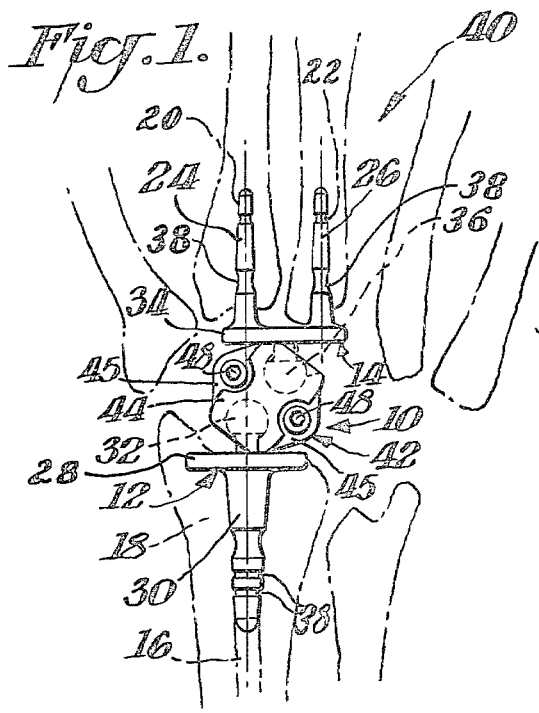
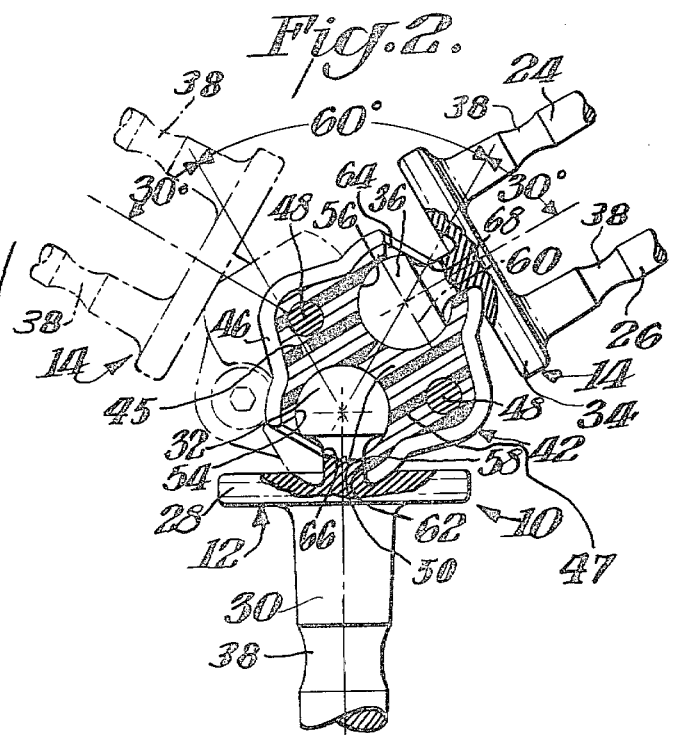
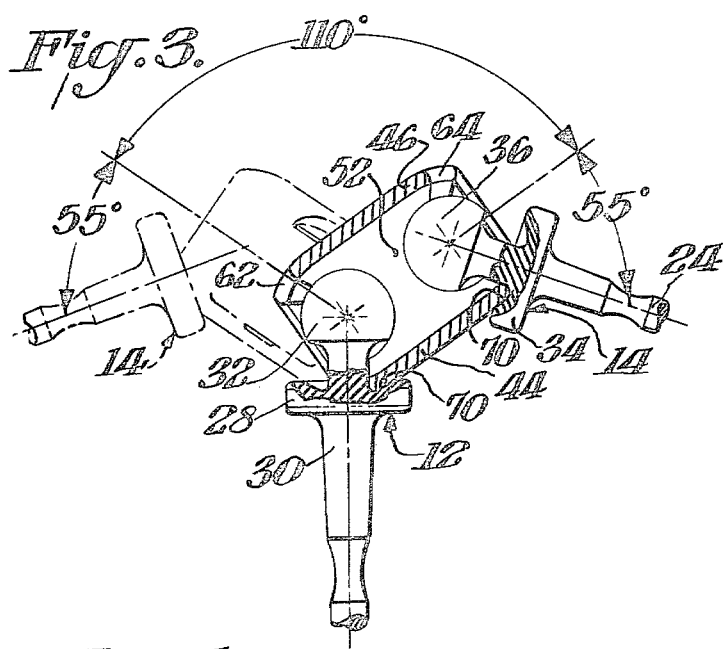
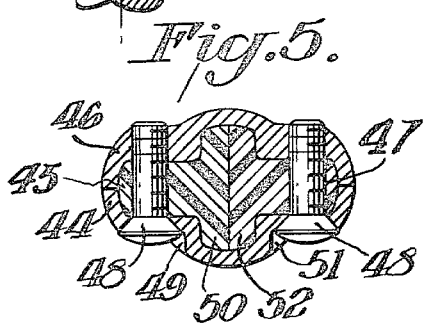
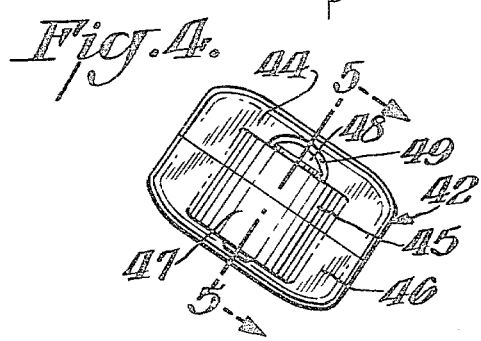

TOTAL TRISPHERICAL WRIST PROSTHESIS

BACKGROUND OF THE INVENTION

Trispherical prosthetic shoulder devices are described in U.S. Pat. Nos. 4,003,095 and 4,040,131 by this same inventor. An object of this invention is to provide a total prosthesis replacement for the wrist which is anatomically compatible and has an adequate range of movement.

SUMMARY

In accordance with this invention the prosthesis includes two components having biocompatible metal balls at one end thereof. The radial component is secured by an affixation to the distal radius. The metacarpel component is implanted by a pair of affixation stems into the second and third metacarpel bones of the hand. The balls are rotatably captured between a pair of cutout plastic polygonal blocks clamped together by a biocompatible metal shell, which is spacially compatible within the wrist area. The range of motion is in excess of normal wrist motion and the components are positively retained.

BRIEF DESCRIPTION OF THE DRAWINGS

Novel features and advantages of the present invention will become apparent to one skilled in the art from a reading of the following detailed description in conjunction with the accompanying drawings wherein similar reference characters refer to similar parts and in which:

FIG. 1 is a view in elevation showing an embodiment of this invention implanted between the distal radius of the arm and the second and third metacarpels of the hand;

FIG. 2 is a cross-sectional view taken through the prosthesis shown in FIG. 1 showing the articulating limits of the radio-ulnar motion;

FIG. 3 is another cross-sectional view taken through the prosthesis shown in FIG. 1 showing the articulation limits of the dorso-volar motion;

FIG. 4 is an end elevation of the shell component shown in FIGS. 1-3; and

FIG. 5 is a cross-sectional view taken through FIG. 4 along the line 5—5.

DESCRIPTION OF THE PREFERRED EMBODIMENT

In FIG. 1 it is shown a total trispherical wrist prosthesis 10 having a ball-headed distal radial component 12 and a ball-headed metacarpel component 14 respectively attached to the intramedullary canal 16 of the distal radius 18 and two internal canals in th second metacarpel bone 20 and the third metacarpel bone 22 by affixation stems 24 and 26. The radial and metacarpel components are made of a biocompatible metal such as Vitallium. Vitallium is a trademark or Howmedica, Inc. for a special coblatchromium alloy developed and used for cast partial and full dentures and for internal applications by surgeons. Cobalt and chromium constitute over 90% of its composition. Vitallium is characterized by a specific gravity of 8.29; tensile strength, 96,000 lb./sq.in. minimum; 2% offset yield strength, 65,000 lb./sq.in. minimum; reduction of area, 8% minimum; elongation, 8% minimum; and modules of elasticity, 30,000,000–32,000,000 lb./sq.in. When polished, it is exceedingly smooth and permanently lustrous. Its outstanding qualities are clinical interness in relation to living tissues and high degree of resistance to corrosion. Radial component 12 has a flange 28 separating tapered stem 30 from ball 32. Metacarpel component 14 has a flange 34 separating tapered stems 24 and 26 from ball 36. Stems 24, 26, and 30 have peripheral grooves 38 to facilitate retention and interlocking with bone cement.

FIG. 1 shows implanted prosthesis 10 disposed between a human radius 16 and hand 40. Its central section or polygonal ball 42 is disposed in the wrist are a and the corresponding bones are removed. The shape of spheroidal section 42 is constructed and arranged to minimize the amount of bone, which must be removed. It is not spheroidal and in the planar viewpoint shown in FIGS. 1 and 2, it somewhat resembles an indented rectangle with triangular shaped extensions 45 and 47, whereas in the edge views shown in FIGS. 3, 4 and 5, it is substantially rectangular. The triangular extensions 45 and 47 along with indented areas 49 and 51 provide mating surfaces and recess areas for self-locking screws 48. It will be referred to herein as polygonal for convenience of description. FIG. 1 shows the outer surface of one hemipolygonal shell 44 of polygonal element 42, which is held together with corresponding shell 46 by a pair of biocompatible self-locking screws 48 also made of Vitallium. Shells 44 and 46 as shown in FIG. 5 clamp together a pair of biocompatible cutout plastic hemipolygonal blocks 50 and 52, which rotatably entrap ball heads 32 and 36 as shown in FIGS. 2 and 3 within sockets 54 and 56. Sockets 54 and 56 extend past the equators 58 and 60 of balls 32 and 36 to positively rotatably retain them.

FIG. 2 shows the articulating limits of the radio-ulnar motion of prosthesis 10. It is 120° in all including 60° about radial ball head 32, and 60° about metacarpel ball head 36.

FIG. 3 shows the articulating limits of the dorso-volar motion of about 220°, which includes 110° about radial ball head 32 and 110° about metacarpel ball head 36. Openings 62 and 64 in shells 44 and 46, neck 66 and 68 of radial and metacarpel components 12 and 14 and concave indentations 70 in radial flange 28 and metacarpel flange 34 cooperate in providing the aforementioned ranges in articulation.

Prosthesis 10 is utilized as follows. The wrist is surgically implanted to restore function of a non-functioning radio-carpal joint affected by disease or trauma. The radial component is inserted and permanently cemented in the intramedullary space of the distal radius. The metacarpel component is inserted and cement into the second and third metacarpel bones of the hand. Both components are retained by the central component with articulation occurring between the respective metal spheres and high density polyethylene plastic.

The components of the trispherical wrist are intensionally constrained to prevent dislocation. This is accomplished by providing an overlapping socket beyond the equator of the mating spherical balls. High pull-out strength is achieved since the plastic element is enclosed and supported within a Vitallium[R] shell.

The wrist prosthesis is assembled after both components are cemented in place. The plastic components are then installed, the two metal shells are assembled, and the assembly is completed by the tightening of two self-locking cap screws.

Special features of the trispherical wrist are:

(a) The range of motion is in excess of normal wrist motions (e.g. radio-ulnar and dorso-volar motion).
(b) The components are mechanically retained (non-constrained design) to prevent dislocation. This design feature essentially replaces the constraining function normally provided by the viable ligaments of the hand.
(c) The assembly is anatomically configured; thereby requiring minimum bone removal.

I claim:

1. A total trispherical prosthetic wrist device comprising a ball-headed radial component of a biocompatible metal, a radial stem on the ball-headed radial component for affixing it to the intramedullary canal of the distal radius, a radial flange separating the ball head of the radial component from its stem, a ball-headed metacarpel component of a biocompatible metal, a pair of metacarpel stems on the metacarpel component for affixing it to a pair of metacarpel bones of the hand, a metacarpel flange means separating the metacarpel ball from the metacarpel stems, a polygonal ball-capturing member having a pair of spherical sockets disposed substantially 180° from each other, the ball-capturing member comprising a pair of biocompatible cutout plastic hemipolygonal blocks sharing the sockets between them, clamping means joining the hemipolygonal bolcks together whereby the ball heads are rotatably trapped in the sockets to provide a substantially stable wrist prosthesis with substantially wide range of movement, the clamping means comprising a pair of metal elongated rectangular shells having longer sides and shorter ends with the ball heads extending through the shorter ends, the clamping means substantially surrounding the hemipolygonal blocks whereby the shells are spacially compatible within the wrist area and provide a range of motion in excess of normal, and fastening means joining the metal shells together.

2. A total trispherical prosthetic wrist device as set forth in claim 1, wherein the metacarpel stems are constructed and arranged for affixation to the second and third metacarpel bones of the hand.

3. A total trispherical prosthetic wrist device as set forth in claims 1 or 2, wherein the pair of metacarpel stems are affixed to a single metacarpel flange.

4. A total trispherical prosthetic wrist device as set forth in claim 1, wherein the device has a radio-ulnar range of motion of about 120°.

5. A total trispherical prosthetic wrist device as set forth in claim 4, wherein the radio-ulnar range of motion is comprised of about 60° about the ball of the radial component and about 60° about the ball of the metacarpel component.

6. A total trispherical prosthetic wrist device as set forth in claim 1, wherein the device has a dorso-volar range of motion of about 220°.

7. A total trispherical prosthetic wrist device as set forth in claim 6, wherein the range of motion about the ball of the radial component is about 110° and the range of motion about the ball of the metacarpel component is about 110°.

8. A total trispherical prosthetic wrist device as set forth in claim 1, wherein the shape of the ball-capturing member in planar configurations of the wrist is polygonal.

9. A total trispherical prosthetic wrist device as set forth in claim 8, wherein the shape of the ball capturing member on edge to planar configurations of the wrist is relatively flat.

* * * * *